US00PP37057P3

(12) United States Plant Patent
Deng

(10) Patent No.: US PP37,057 P3
(45) Date of Patent: Oct. 21, 2025

(54) ***CALADIUM* PLANT NAMED 'UF-15-23'**

(50) Latin Name: ***Caladium* x *hortulanum***
Varietal Denomination: UF-15-23

(71) Applicant: Florida Foundation Seed Producers, Inc., Marianna, FL (US)

(72) Inventor: Zhanao Deng, Riverview, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 19/032,777

(22) Filed: Jan. 21, 2025

(65) Prior Publication Data

US 2025/0241217 P1 Jul. 24, 2025

Related U.S. Application Data

(60) Provisional application No. 63/623,981, filed on Jan. 23, 2024.

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/12
See application file for complete search history.

(56) References Cited

PUBLICATIONS https://journals.ashs.org/hortsci/view/journals/hortsci/59/2/article-p225.xml?tab_body=fulltext; Jan. 16, 2024; 17 pages.*

* cited by examiner

*Primary Examiner* — Kent L Bell
(74) *Attorney, Agent, or Firm* — James R. Holm

(57) ABSTRACT

A new and distinct cultivar of *Caladium* plant named 'UF-15-23', characterized by its very compact growth habit; multiple lance or strap-type leaves that have a creamy background color, slightly ruffled dark green leaf margins, numerous colorful red-purple spots across the leaf blade; blooms with red-purple spots or blotches; moderate resistance to *Fusarium* tuber rot caused by *Fusarium solani*, and suitability for producing pot plants in small containers (4 inches in diameter) from No. 1-sized tubers without tuber de-eyeing.

6 Drawing Sheets

CROSS-REFERENCE TO RELATED APPLICATIONS

This Application is related to and claims the benefit of U.S. Provisional Patent Application Ser. No. 63/623,981 filed on Jan. 23, 2024, entitled *CALADIUM* CULTIVARS, the entirety of which is incorporated herein by reference.

Genus and species: *Caladium* x *hortulanum*.

Cultivar denomination: 'UF-15-23'.

BACKGROUND OF THE NEW CULTIVAR

The present invention relates to a new and distinct cultivar of *Caladium*, botanically known as *Caladium* x *hortulanum*, and hereinafter referred to by the name 'UF-15-23'. *Caladium* plants are tuberous-rooted plants and typically have attractive heart-shaped or arrow-shaped leaves on long stalks rising directly from the tubers. Foliage may grow in a variety of colors and variegation patterns, and many species have been developed for aesthetic coloration, good container and landscape growth, drought tolerance, pest resistance, and other desirable characteristics.

Plant Breeder's Rights for this cultivar have not been applied for.

SUMMARY OF THE INVENTION

The new *Caladium* cultivar 'UF-15-23' has not been observed under all possible environmental conditions. The phenotype of the new cultivar may vary with variations in environment and cultural practices such as temperature, light intensity, fertilization, irrigation, and application of plant growth regulators without any change in genotype.

The objective of the breeding program that produced the present cultivar was to develop cultivars that have novel foliar characteristics, produce multiple brightly colored leaves, have good tuber yield potential, and perform well in containers and the landscape. The present *Caladium* cultivar originated from a cross-pollination made in July 2012 in Wimauma, Florida between the *Caladium* x *hortulanum* breeding line 'UF 317' (unpatented), as the female or seed parent, and the *Caladium* x *hortulanum* cultivar 'Gingerland' (unpatented), as the male or pollen parent. The new *Caladium* cultivar was discovered and selected by the inventor in September 2015 as a single plant within the progeny of the stated cross-pollination in Wimauma, Florida.

Asexual reproduction of the new cultivar 'UF-15-23' by tuber divisions in a controlled environment has been performed annually in Wimauma, Florida since April 2016. The unique features of this new *Caladium* cultivar are stable and reproduced true to type in successive generations of asexual reproduction.

The new cultivar 'UF-15-23' has not been observed under all possible environmental conditions. The phenotype may vary somewhat with variations in environment such as temperature and light intensity, without, however, any variance in genotype.

The following traits have been repeatedly observed and are determined to be the unique characteristics of 'UF-15-23'. These characteristics in combination distinguish 'UF-15-23' as a new and distinct cultivar of *Caladium:*

1. Very compact, dense and short growth habit;
2. Lance or strap shaped leaves that have a creamy background color, slightly ruffled dark green leaf margins, numerous colorful red-purple spots across the leaf blade, streaked venation throughout the leaves, and blooms with red-purple spots or blotches; and
3. Moderate resistance to *Fusarium solani* tuber rot.

Plants of the new *Caladium* cultivar 'UF-15-23' differ from plants of the female parent 'UF 317', in the following characteristics:

1. Plants of 'UF-15-23' are much shorter than plants of 'UF 317';
2. Leaves of 'UF-15-23' are of the lance or strap type, much smaller, and much narrower, whereas leaves of 'UF 317' are of the fancy type, larger, and broader than 'UF-15-23'; and
3. Petioles of 'UF-15-23' are attached to the base of the leaves and are shorter in length than 'UF 317', whereas petioles of 'UF 317' are attached to the back of the leaves and are longer than 'UF-15-23'.

Plants of the new *Caladium* cultivar 'UF-15-23' differ from plants of the male parent and commercial *Caladium* cultivar, 'Gingerland', in the following characteristics:

1. Plants of 'UF-15-23' are shorter, narrower, and more compact than plants of 'Gingerland';
2. Leaves of 'UF-15-23' are much shorter and narrower than leaves of 'Gingerland';
3. Plants of 'UF-15-23' have fewer inflorescences or blooms than plants of 'Gingerland'; and
4. Blooms of 'UF-15-23' have red-purple spots or blotches on the spathe, whereas these red-purple spots or blotches are not present on spathes of 'Gingerland'.

Plants of the new *Caladium* cultivar 'UF-15-23' differ from plants of the commercial *Caladium* cultivar 'Cosmic Delight' (U.S. Plant Pat. No. 27,154) in the following characteristics:

1. Plants of 'UF-15-23' are smaller and shorter than plants of 'Cosmic Delight';
2. Leaves of 'UF-15-23' have a whiter center and a darker green border than leaves of 'Cosmic Delight';
3. Spots on leaves of 'UF-15-23' are darker, more in number, and much more vibrant in color than the spots on leaves of 'Cosmic Delight'; and
4. Petioles of 'UF-15-23' are distinctively darker near the leaf attachment, whereas petioles of 'Cosmic Delight' are lighter near the leaf attachment.

DESCRIPTION OF THE FIGURES

The accompanying photographs (as shown in FIGS. 1-6) illustrate the overall appearance of the new *Caladium* cultivar 'UF-15-23'. These photographs show the colors as true as can be reasonably obtained in colored reproductions of this type. Colors in the photographs may differ slightly from the color values cited in the detailed botanical description, which accurately describe the colors of the new *Caladium* cultivar.

DETAILED BOTANICAL DESCRIPTION OF THE CULTIVAR

Figure 1:
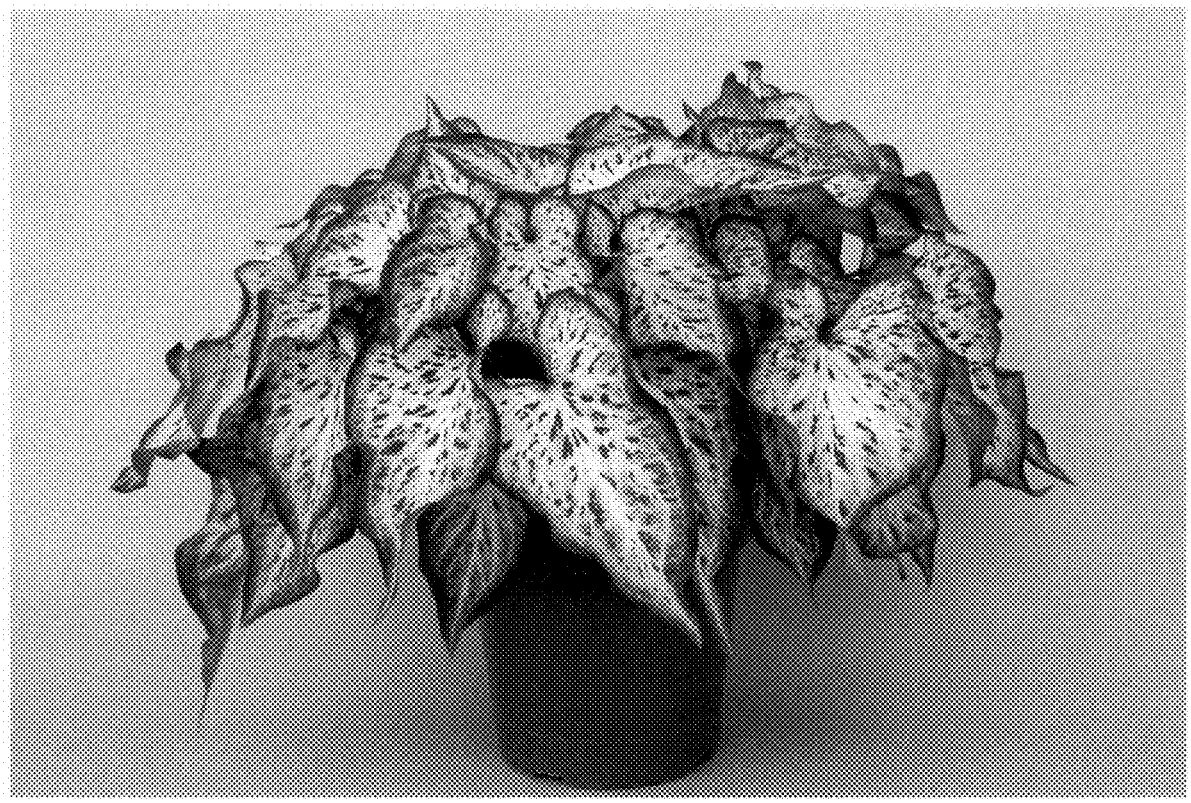
FIG. 1 shows a side perspective view of a typical plant of 'UF-15-23' grown in a container in a greenhouse.
Figure 2:
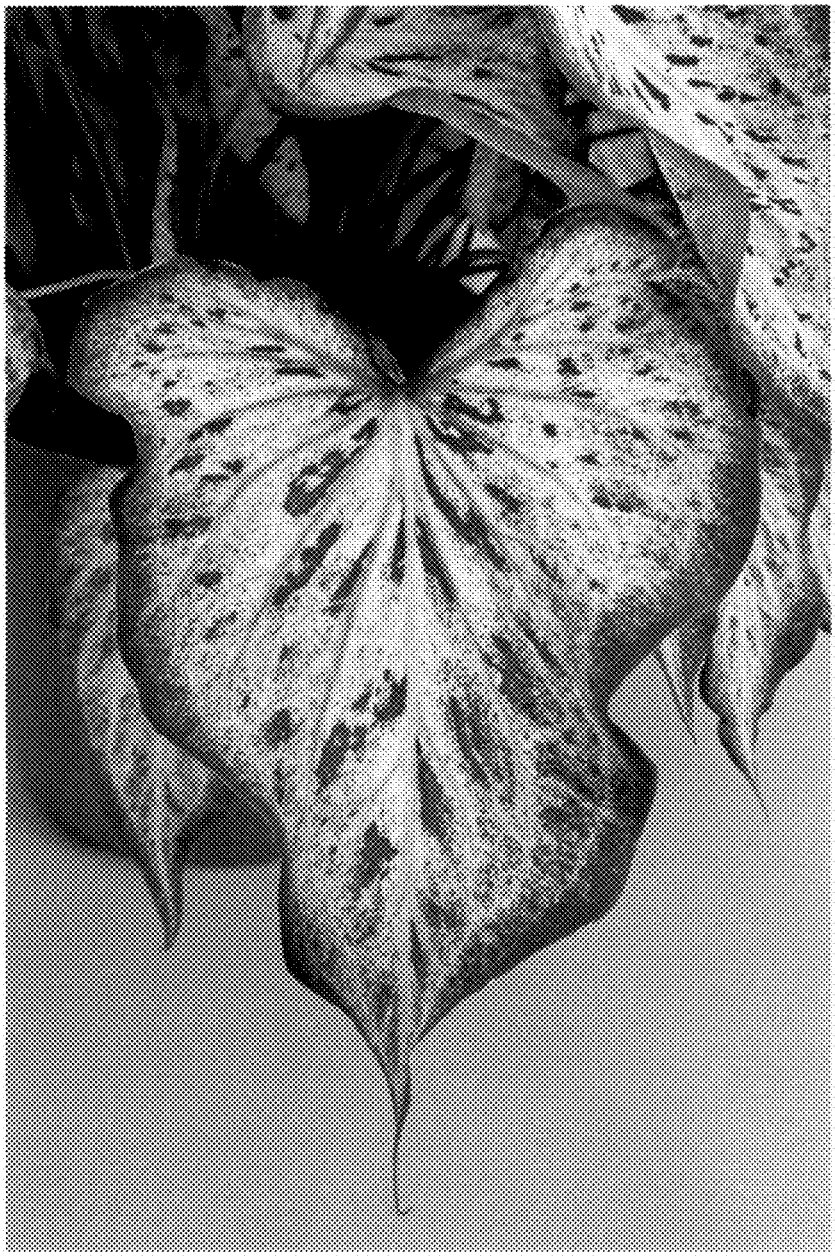
FIG. 2 shows a close-up view of a typical leaf of 'UF-15-23' grown in a container in a greenhouse.
Figure 3:
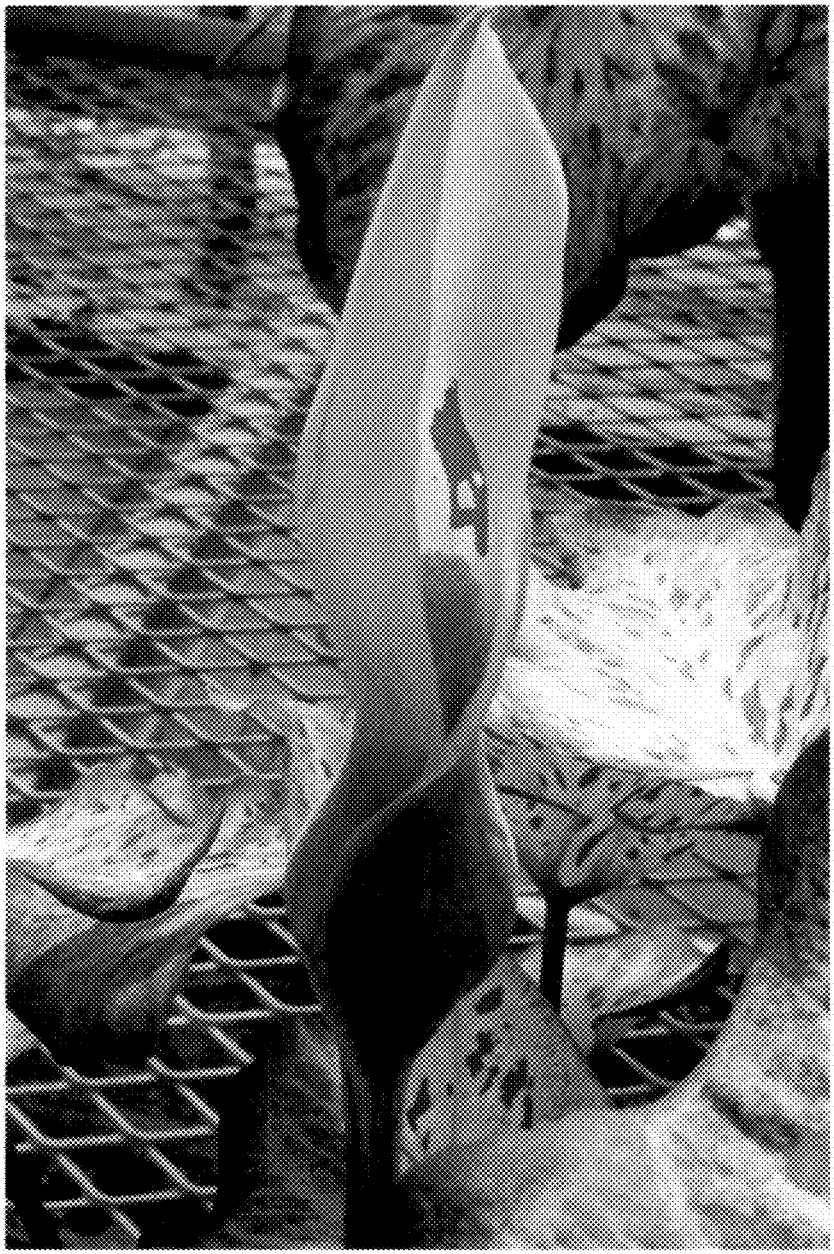
FIG. 3 shows a close-up view of a typical bloom of 'UF-15-23' grown in a container in a greenhouse.
Figure 4:
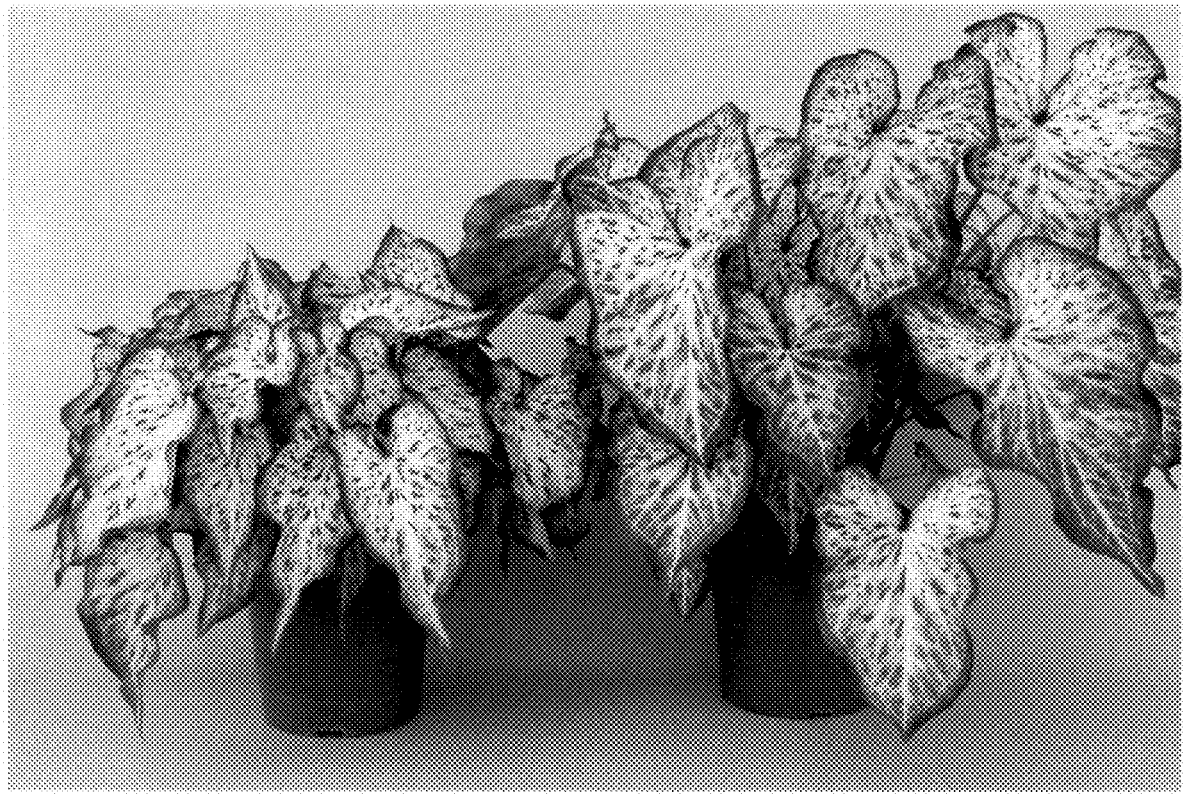
FIG. 4 shows a side perspective view of typical plants of 'UF-15-23' (left) and the pollen parent 'Gingerland' (right) grown in containers in a greenhouse.
Figure 5:
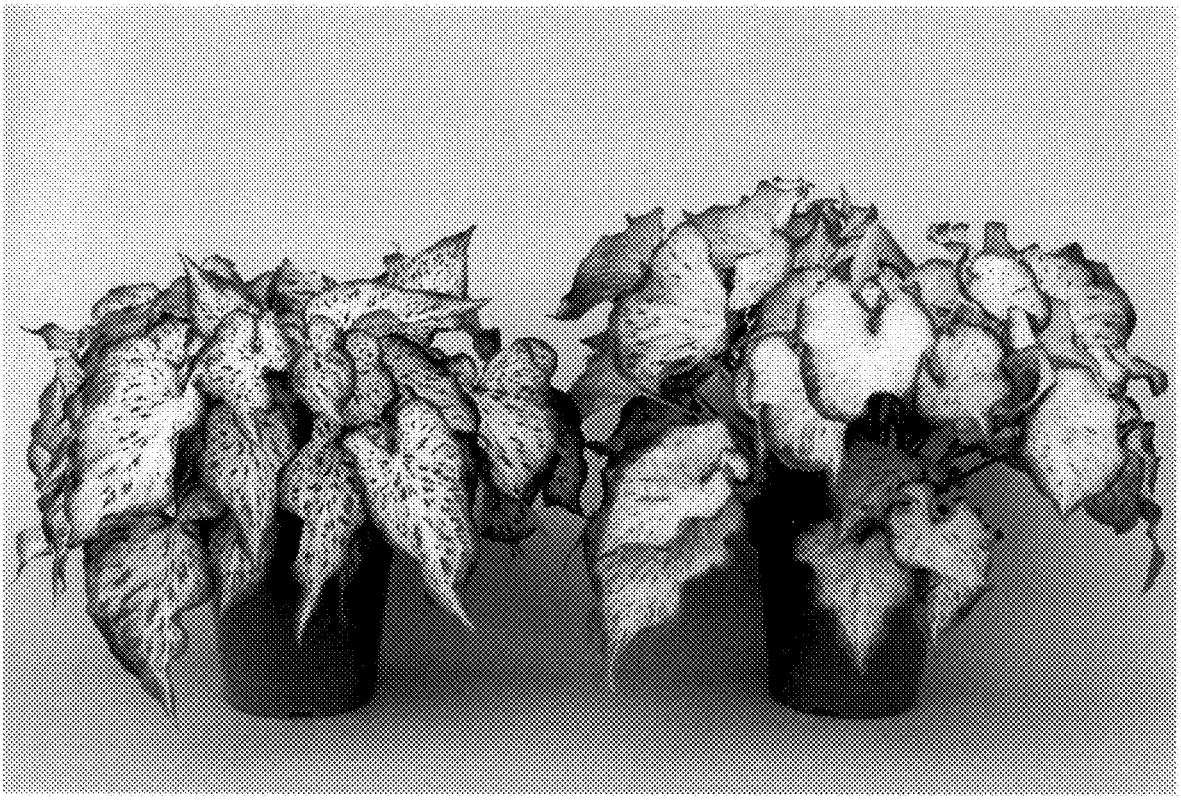
FIG. 5 shows side perspective view of typical plants of 'UF-15-23' (left) and 'Cosmic Delight' (right) grown in containers in a greenhouse.
Figure 6:
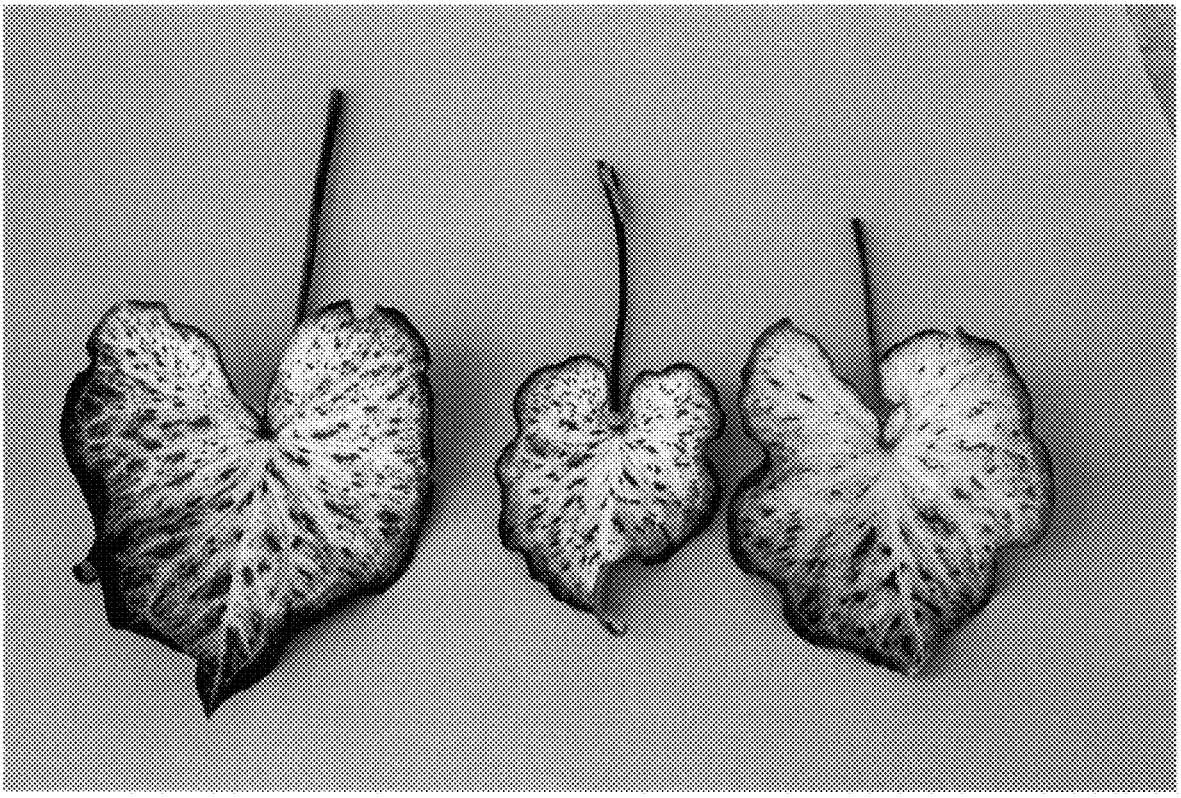
FIG. 6 shows a close-up view of typical leaves of the pollen parent 'Gingerland' (left), 'UF-15-23' (center), and 'Cosmic Delight' (right) grown in containers in a greenhouse.

In the following description, color references are made to The Royal Horticultural Society (R.H.S.) Colour Chart, 2001 Edition, except where general terms of ordinary dictionary significance are used.

DESCRIPTION OF GROWING CONDITIONS

The aforementioned photographs and the following observations and measurements describe plants grown in 8-inch containers in Wimauma, Florida during the summer in a polypropylene-covered shade house and also describe plants grown in an outdoor nursery in ground beds in Wimauma, Florida during the late summer. All plants were grown under conditions and practices that approximate those generally used in commercial *Caladium* production.

During the production of the plants, day temperatures ranged from about 26° C. to 35° C., night temperatures ranged from about 18° C. to 26° C. and light levels ranged from 2400 to 3840 foot-candles in the greenhouse to 8300 foot-candles for plants grown in the outdoor nursery. Plants grown in the greenhouse were about 6 weeks old from tubers when the photographs and the detailed description were taken. Plants grown in the outdoor nursery were about 3 months old from tubers when the photographs and the detailed description were taken.

BOTANICAL DESCRIPTION

Botanical classification:

*Family.*—Araceae.

*Botanical name.*—*Caladium* x *hortulanum.*

*Common name.*—*Caladium* or *Caladium.*

*Cultivar.*—'UF-15-23'.

Parentage:

*Female or seed parent.*—*Caladium* x *hortulanum* breeding line 'UF 317' (unpatented).

*Male or pollen parent.*—*Caladium* x *hortulanum* cultivar 'Gingerland' (unpatented).

Propagation:

*Type.*—By tubers and by tuber divisions.

*Time to initiate roots, summer.*—About seven to ten days at 32° C.

*Time to initiate roots, winter.*—About two to three weeks at 24° C.

Tuber description:

*Number of buds per tuber* (*greenhouse-grown plants*).—About 5 to 8 actively growing buds/shoots.

*Number of buds per tuber* (*outdoor nursery-grown plants*).—About 4 to 6 actively growing buds/shoots.

*Height*.—2.5 cm.

*Diameter*.—3.7 cm.

*Texture*.—Thick, starchy, and somewhat brittle.

*Color*.—Epidermis: 200A (brown). Interior: 14B (yellow-orange) with edges more 14C (yellow).

Root description: Dense, thick, and white fleshy roots.

Plant description:

*Type*.—Herbaceous perennial.

*Growth habit*.—Compact, short plant habit suitable for 4-inch to 10-inch containers and garden beds.

*Leaf petioles*.—Arising from tubers, mostly upright, curving outwardly with development.

*Plant height, from soil level to top of leaf plane*.—Greenhouse grown plants: Average 28.0 cm. Outdoor nursery grown plants: Average 23.3 cm.

*Plant height, from soil level to top of the inflorescences*.—Greenhouse grown plants: Average 29.5 cm. Outdoor nursery grown plants: No inflorescences observed.

*Plant diameter or spread*.—Greenhouse-grown plants: Average 62.5 cm. Outdoor nursery grown plants: Average 46.3 cm.

Foliage description:

*Length*.—Greenhouse grown plants: Average 20.9 cm. Outdoor nursery grown plants: Average 16.4 cm.

*Width* (*flattened*).—Greenhouse grown plants: Average 13.6 cm. Outdoor nursery grown plants: Average cm 10.1 cm.

*Shape*.—Lance or strap-type.

*Apex*.—Acuminate.

*Base*.—Cordate.

*Margin*.—Entire and undulate.

*Texture*.—Upper surface: Smooth, glabrous. Lower surface: Smooth, glabrous; glaucous.

*Venation pattern*.—Pinnate.

*Color, developing leaves* (*greenhouse grown plants*).—Upper surface: Center: 155A white, heavily speckled with 137B (green) and pronounced and densely distributed spots of 61A (red-purple) spots. Borders and margins: A thin edge of 137A (green) and 58A (red-purple) along the extreme edge between upper and lower leaf surface. Basal notch: Not obvious. Venation: Mid rib: 155A (white). Primary veins: 155A (white) with some streaking of 61A and 61B (red-purple). Lower surface: Center: 137D (green) with a small amount of 155A (white) near the veins with numerous spots of 71A (red-purple). Border and margins: 138A (green) with an extremely thin edge of 58A (red-purple). Venation: Midrib: 139D (green) with streaks of 61B (red-purple). Primary veins: 139C (green).

*Color, fully expanded leaves* (*greenhouse grown plants*).—Upper surface: Center: 155A (white) and heavily speckled with 137B and 137C (green) with pronounced and densely distributed spots of 61A (red-purple). Borders and margins: 137A (green) along the edge and 58A (red-purple) along the extreme edge between upper and lower leaf surface. Basal notch: 61C (red-purple). Venation: Mid rib: 155A (white). Primary veins: 155A (white) with some streaking of 61A and 61B (red-purple). Lower surface: Center: 155A (white) with speckles of 137D (green). Border and margins: 139B (green) with very thin edge of 58A (red-purple). Venation: Mid rib: 199D (grey-brown) with streaks of 61B (red-purple). Primary veins: 138B (green) with a few streaks of 61B (red-purple).

*Color, developing leaves* (*outdoor nursery grown plants*).—Upper surface: Center: 138B and 138C (green). Border and margins: 139A and 139B. Venation, mid rib and primary veins: Extremely thin 61A (red-purple), mid rib and primary veins are not prominent. Lower surface: Center: 137D (green). Border and margins: 138A and 138B (green) with an extremely thin edge of 58A (red-purple). Venation: Midrib: 139C (green) with a slight coloration of 58A (red-purple). Primary veins: 139B (green).

*Color, fully expanded leaves* (*outdoor nursery grown plants*).—Upper surface: Center: 155A (white) with a background heavily speckled with 137B and 137C (green) and many splotches of 61A (red-purple). Border and margins: 137A (green). Venation: Midrib: 155A (white) with streaks of 61B (red-purple). Primary veins: 61A and 61B (red-purple). Lower surface: Center: 155A (white) with a prominent background coloration of 137D (green) and splotches of 61A (red-purple). Border and margins: 139B (green) with a very thin edge of 58A (red-purple). Venation: Midrib: 186B and 186C (greyed-purple). Primary veins: 138B (green).

*Petiole*.—Aspect: Mostly erect, curving outwardly with development. Length: Greenhouse grown plants: Average 19.8 cm. Outdoor nursery grown plants: Average 19.3 cm. Diameter, distal: Greenhouse grown plants: Average 4.3 mm. Outdoor nursery grown plants: Average 2.9 mm. Diameter, proximal: Greenhouse grown plants: Average 7.1 mm. Outdoor nursery grown plants: Average 4.0 mm. Strength: Strong and flexible. Color: Greenhouse grown plants: 200B (brown) and lighter near the leaf base to 199D (grey-brown) with streaks of 61B (red-purple). Outdoor nursery grown plants: 200A (brown) becoming 186C (greyed-purple) nearest to the leaf. Wing length: Greenhouse grown plants: Average 5.2 cm. Outdoor nursery grown plants: Average 4.1 cm. Wing diameter: Greenhouse grown plants: Average 7.8 mm. Outdoor nursery grown plants: Average 5.1 mm. Wing color: Greenhouse grown plants: 63D (red-purple) with streaks of 200B (brown). Outdoor nursery grown plants: 63D (red-purple) with streaks of 200B (brown).

Inflorescence description: Only observed on greenhouse-grown plants.

*Arrangement*.—Upright hooded spathes surrounding a columnar spadix borne on a tall upright scape. Spadix with sessile, simple female and male flowers separated into two zones: female flowers arranged on the lower one-third of the spadix, male flowers arranged on the upper two-thirds of the spadix. Sterile flowers develop between female and male flower zones; near this area, the spathe constricts surrounding the female flowers.

*Fragrance*.—None detected.

*Natural flowering season*.—'UF-15-23' typically flowers during the spring or early summer in central Florida; flowers develop about seven weeks after growth commences and inflorescences last about three days before fading, inflorescences are persistent.

*Spathe*.—Length: Average 11.2 cm. Width, distal: 2.5 cm. Width, proximal: 2.0 cm. Shape: Ovate to somewhat obovate. Apex: Acute to acuminate. Base: Tapering. Margin: Entire. Texture, upper and lower surfaces: Smooth, glabrous. Color: Front surface: Upper two-thirds: 159C (orange-white) to 160D (greyed-yellow) with thin streaks of 143C (green) in center with a few splotches of 60B (red-purple). Lower one-third: 143A and 143B (green). Rear surface: Upper two-thirds: 160B and 160C (greyed-yellow) with streaks of 143C (green) and 161C (greyed-yellow), and blotches of 60C and 60D (red-purple). Lower one third: 143C (green).

*Spadix*.—Length, entire spadix: Average 7.8 cm. Shape: Spindle-shaped to columnar. Apex: Obtuse. Base: Obtuse. Aspect: Upright. Male flower zone: Length: Average 5.0 cm. Diameter: Average 8.5 mm. Color, mature: 158B (orange-white). Male flowers: Quantity per spadix: Average 126. Shape: Obovate. Height: Average 3.9 mm. Diameter: Average 3.2 mm. Anthers: Close to 160C (greyed-yellow). Pollen amount: Good, moderate. Sterile flower zone: Length: Average 1.8 cm. Diameter: Average 6.6 mm. Color, mature: 158B (orange-white). Female flower zone: Length: Average 1.0 cm. Diameter: Average 5.4 mm. Color: 9D (yellow). Female flowers: Quantity per spadix: Average 77. Shape: Obovate. Height: Average 1.9 mm. Diameter: Average 1.7 mm. Stigma color: 159D (orange-white) to 160A (greyed-yellow). Ovary color: 159A (orange-white) to 160A (greyed-yellow).

*Scape*.—Length: Average 16.8 cm. Diameter: Average 5.2 mm. Strength: Sturdy and flexible. Aspect: Erect. Texture: Smooth, glabrous, glaucous. Color: Mostly 200A (brown) and streaked with 200D (brown) and 199D (grey-brown) with 143C (green) and streaked with 200C and 200D just below the spathe.

*Seeds and fruit*.—Seed and fruit development have not been observed.

Disease and pest resistance: Plants of the new *Caladium* 'UF-15-23' have been observed to be moderately resistant to *Fusarium* tuber rot caused by *Fusarium solani*.

Temperature tolerance: Plants of the new *Caladium* 'UF-15-23' have been observed to be tolerant to temperatures ranging from 7° C. up to about 40° C.

Tuber Yield Potential

The new *Caladium* 'UF-15-23' was also evaluated for tuber production and plant performance at Wimauma, Florida in 2018, 2019 and/or 2020 and compared to plants of the commercial *Caladium* cultivar 'Gingerland'. The soil was an EauGallie fine sand with approximately 1% organic matter and a pH of 6.2. *Caladium* plants were grown in the open field using a plastic mulched, raised bed system. Field plots were organized in a randomized complete block design consisting of three replications. Each plot was 1.2 $m^2$ and contained 30 *Caladium* propagules.

In 2019, field beds were fumigated on February 24 with Pic-Clor 60 at 448 $kg \cdot ha^{-1}$. *Caladium* seed pieces were planted on April 4. Fifty pounds of granular nitrogen (50 N) per acre was incorporated into the soil prior to bedding. Fertigation began on June 1 by injecting a commercial liquid fertilizer (5N-0.87P-6.64K) at 0.454 kg of nitrogen an acre a day. The fertilization rate was increased to 0.908 kg of nitrogen an acre a day on beginning on July 24 and ended on October 31. Tubers were dug and washed on December 9 and dried in the greenhouse for approximately 45 days. Tubers were graded by the maximum diameter: Mammoth (8.9 to 11.4 cm), Jumbo (6.4 to 8.9 cm), No. 1 (3.8 to 6.4 cm), and No. 2 (2.5 to 3.8 cm). Tuber grades and counts were converted into a production index to show the relative economic value of the harvested tubers per field plot: Production index=6n (Mammoth)+4n (Jumbo)+2n (No. 1)+1n (No. 2), where n=number of tubers in the grade. The relative values assigned to the five tuber grades in calculating production index were based on the relative market prices provided by Florida *Caladium* tuber producers.

In the 2020 season, ground beds were fumigated on February 12 with Pic-Clor 60 at 448 $kg \cdot ha^{-1}$. *Caladium* seed tubers were treated in hot water (50° C.) for 30 minutes. Seed tuber pieces were dusted with RootShield® Plus WP and planted manually on April 15 with the same in-row and between-row spacing as in 2019. Two drip tapes were buried under the plastic mulch along the raised beds to provide the irrigation water and fertilization. Fertigation began on May 28 by injecting a commercial liquid fertilizer (5N-0.87P-6.64K) at the rate of 0.454 kg of nitrogen an acre a day and ended on October 30. Tubers were dug and washed on December 1-2, dried in the greenhouse for approximately 63 days, and weighed, graded, and counted on Feb. 3, 2021.

The tuber weight, marketable tubers, and production index of 'UF-15-23' were not significantly different from 'Gingerland' in 2019 (Table 1), but the tuber weight, marketable tubers, and production index of 'UF-15-23' were 112%, 279%, or 150% greater than those of 'Gingerland' in 2020, respectively (Table 1). 'UF-15-23' may have higher tuber yield potential than 'Gingerland'. The primary grade of tubers produced by 'UF-15-23' was No. 2 (48.7% in 2019 and 74.5% in 2020), followed by No. 1 (45.8% in 2019 and 22.9% in 2020). 'UF-15-23' produced more No. 1 tubers than Gingerland in 2019 (Table 1).

As shown in Table 1, tuber weight, marketable number, production index, and grade distribution of 'UF-15-23' are compared to the commercial *Caladium* cultivar 'Gingerland' in replicated experimental field plots in 2019 and 2020 in Wimauma, Florida. Values presented are means of three plots with 30 propagules planted in a plot of 1.2 $m^2$.

TABLE 1

Tuber weight, marketable number, production index, and grade distribution

| | Tuber | | | Tuber grade distribution (%) | | |
|---|---|---|---|---|---|---|
| | Weight (kg) | Marketable (no.) | Production index | Jumbo | No. 1 | No. 2 |
| Cultivar | 2019 | | | | | |
| 'UF-15-23' | 1.20 | 29.0 | 48 | 5.5 | 45.8 a | 48.7 |
| 'Gingerland' | 0.73 | 23.7 | 33 | 1.2 | 19.6 b | 79.2 |
| P value | .2465 | .3564 | .2985 | .2225 | .0326 | .0530 |
| | 2020 | | | | | |
| 'UF-15-23' | 1.40 a | 52.0 a | 75 a | 2.5 | 22.9 | 74.5 |
| 'Gingerland' | 0.66 b | 13.7 b | 30 b | 4.9 | 22.0 | 73.1 |
| P value | .0159 | .0296 | .0202 | .3266 | .8485 | .8154 |

Additional Plant Comparisons

Plants of the new *Caladium* 'UF-15-23' were evaluated for growth, leaf color display, sunburn tolerance, and leaf health in the same field plots that were used for evaluating tuber production potential. A scale of 1 to 5 was used for rating plant growth, with 1 being very poor (few leaves and lack of vigor) and 5 being excellent (full plants, numerous leaves). A scale of 1 to 5 was used for rating leaf color display, with 1 being very poor (dull or bleached, lack of color display) and 5 being excellent (bright, very attractive). Sunburn tolerance was evaluated on a scale of 1 to 5, with 1 being very susceptible to sunburn (leaves having numerous sun-damaged areas or holes) and 5 being resistant to sunburn (no visible sun-damaged areas). Leaf health was evaluated on a scale of 1 to 5, with 1 being numerous diseased spots and completely unsightly and 5 being healthy and free of visible leaf spot disease. Evaluations of plant growth, leaf color, sunburn tolerance and leaf health were done on July 13, August 13, September 19 of 2019; and July 31, August 21, and September 25 of 2020.

Plants of the new *Caladium* 'UF-15-23' received a score of 1.3 to 4.0 for their growth in seven evaluations in 2019 and 2020 (Table 2). These scores were relatively low but were significantly higher than those of its male or pollen parent 'Gingerland' (1.2 to 2.5) in one of the three evaluations in 2019 and two of the four evaluations in 2020, indicating improved plant growth than 'Gingerland'.

Leaf color scores of the new *Caladium* 'UF-15-23' were between 2.8 and 4.2, higher than the leaf color scores of 'Gingerland' in two out of the seven evaluations (Table 2). Plants of 'UF-15-23' showed good to excellent sunburn tolerance in both 2019 and 2020 growing seasons, with sunburn tolerance ratings between 3.7 and 4.8 (Table 2). Its sunburn tolerance ratings were not significantly different from those of 'Gingerland' (3.8 to 4.8) in all seven evaluations. The leaf health score of 'UF-15-23' ranged from 2.3 to 4.8 in 2019 and from 3.5 to 4.5 in 2020. 'UF-15-23' received a higher leaf health score than 'Gingerland' in one evaluation.

As shown in Table 2, plant growth, leaf color, sunburn tolerance, and leaf health ratings of the new *Caladium* 'UF-15-23' are compared to the commercial *Caladium* cultivar 'Gingerland' (check) grown from 2.5-cm tuber propagules in ground beds in full sun in Wimauma, FL. Plant growth, leaf color, sunburn tolerance, and leaf health rating values are means of three plots based on whole plot evaluation in each evaluation.

TABLE 2

Plant growth, leaf color, sunburn tolerance, and leaf health ratings

| | Plant Growth Ratings | | | | | | |
|---|---|---|---|---|---|---|---|
| | 2019 | | | 2020 | | | |
| Cultivars | July | August | September | July | August | September | October |
| 'UF-15-23' | 2.7 | 2.8 a | 1.3 | 2.3 a | 2.2 | 4.0 a | 2.5 |
| 'Gingerland' | 2.5 | 1.5 b | 1.2 | 1.3 b | 1.3 | 2.0 b | 1.5 |
| p value | .4226 | .0012 | .7418 | .0377 | .0742 | .0427 | .0742 |
| | Sunburn Tolerance Rating | | | | | | |
| | 2019 | | | 2020 | | | |
| Cultivars | July | August | September | July | August | September | October |
| 'UF-15-23' | 4.8 | 4.3 | 3.8 | 4.5 | 4.5 | 3.7 | 3.8 |
| 'Gingerland' | 4.8 | 4.0 | 3.8 | 4.2 | 4.2 | 4.0 | 3.8 |
| p value | | . 1835 | | .1835 | .1835 | .4226 | |
| | Leaf Color Rating | | | | | | |
| | 2019 | | | 2020 | | | |
| Cultivars | July | August | September | July | August | September | October |
| 'UF-15-23' | 4.2 | 4.2 | 2.8 | 3.8 a | 3.8 a | 3.2 | 3.7 |
| 'Gingerland' | 3.2 | 3.2 | 2.7 | 2.7 b | 3.0 b | 3.0 | 3.0 |
| p value | .0742 | .0742 | .4226 | .0198 | .0377 | .4226 | .0572 |
| | Leaf Health Rating | | | | | | |
| | 2019 | | | 2020 | | | |
| Cultivars | July | August | September | July | August | September | October |
| 'UF-15-23' | 4.8 | 4.3 a | 2.3 | 4.5 | 4.0 | 3.5 | 3.8 |
| 'Gingerland' | 4.3 | 1.7 b | 2.8 | 3.8 | 3.2 | 2.3 | 3.7 |
| p value | .2254 | .0263 | .4226 | .0572 | .1994 | .1181 | .1181 |

Container Trials

The new *Caladium* 'UF-15-23' was evaluated and compared to its male or pollen parent 'Gingerland' for suitability for container plant production. The evaluation was conducted in 2020 by forcing dried tubers in 12.7-cm containers (diameter). No. 1-sized tubers (intact or de-eyed) were planted on May 1, 2020 in a commercial potting mix amended with Osmocote® fertilizer (15N-3.9P-10K, 5-6 months) at 4.3 $kg \cdot m^{-3}$ and Micromax® at 0.48 $kg \cdot m^{-3}$ Potted tubers and plants were grown in a greenhouse with approximately 30% light exclusion. Temperatures in the greenhouse ranged from 25° C. (night) to 33° C. (day). Potted tubers and plants were arranged on metal benches, with a pot-to-pot spacing of 0.4 meters, in the greenhouse in a randomized complete block design with six replicates. Fungicide Subdue® Maxx and insecticide Neemix® were applied as a drench to all potted plants. Plant height, plant width, number of leaves, and foliar characteristics were recorded approximately 8 weeks after planting. Quality of the potted *Caladium* plants was rated on a scale of 1 to 5, with 1=very poor, unattractive, totally unacceptable as potted plants with few leaves, and 5=very attractive, full plants with a symmetrical shape, an appropriate height, and many bright, colorful leaves.

Intact tubers of the new *Caladium* 'UF-15-23' sprouted about 32 days after planting, approximately 17 days later than 'Gingerland' (Table 3). Plants forced from intact tubers had an average height of 21.7 cm, an average width of 38.8 cm, an average of 13.2 leaves, and the leaves were averaged to be 19.8 cm long and 12.8 cm wide. Thus, plants of 'UF-15-23' forced from intact tubers and grown for 8 weeks were 18 cm shorter, 6.5 cm narrower, and leaves were 7.3 cm shorter, and 5.4 cm narrower than 'Gingerland'.

De-eyed tubers of 'UF-15-23' sprouted about 33 days after planting, approximately 8 days later than 'Gingerland'. Plants of 'UF-15-23' forced from de-eyed tubers were 21.8 cm tall and 39.7 cm wide and had about 15 leaves per plant, and leaves were 16.0 cm long and 10.0 cm wide. Compared to 'Gingerland' plants from de-eyed tubers, 'UF-15-23' plants from de-eyed tubers were 4.9 cm shorter and had fewer leaves (15.2 vs. 28.8). Plants of 'UF-15-23' from intact and de-eyed tubers received a quality rating of 3.1 or 3.2, indicating that these plants met the required quality for potted *Caladium* plants. These results indicate that 'UF-15-23' is slower to sprout than 'Gingerland' but it does not need additional time for production of prefinished or finished container plants. In addition to producing more compact plants in containers, 'UF-15-23' had fewer blooms (0 to 0.2 vs. 1.2 to 1.7 per plant) than 'Gingerland'.

As shown in Table 3, days to sprout, plant height and width, leaf number, length and width, number of blooms (inflorescences), and plant quality ratings of the new *Caladium* 'UF-15-23' are compared to the commercial *Caladium* cultivar 'Gingerland' grown in small containers. No. 1 tubers were planted in 12.7-cm containers (one tuber per container) and grown in a shaded glasshouse in Wimauma, FL in 2020. Values represent the means of six plants (replicates) produced from intact or de-eyed No. 1 (3.8 to 6.4 cm in diameter) tubers planted individually per container.

TABLE 3

Days to sprout, plant height and width, leaf number, length and width, number of blooms (inflorescences), and plant quality ratings

| | Days to Sprout | | Plant Height (cm) | |
|---|---|---|---|---|
| Cultivar | Intact | De-eye | Intact | De-eye |
| 'UF-15-23' | 32.3 a | 32.7 a | 21.7 b | 21.8 b |
| 'Gingerland' | 15.2 b | 24.2 b | 39.7 a | 26.7 a |
| P value | .0002 | .0001 | .0101 | .0334 |
| | Leaf Length (cm) | | Leaf Width (cm) | |
| | Intact | De-eye | Intact | De-eye |
| 'UF-15-23' | 19.8 b | 16.0 | 12.8 b | 10.0 |
| 'Gingerland' | 27.1 a | 16.5 | 18.2 a | 9.8 |
| P value | .0006 | .4155 | .0003 | .8319 |
| | Plant Width (cm) | | Leaves (no.) | |
| Cultivar | Intact | De-eye | Intact | De-eye |
| 'UF-15-23' | 38.8 b | 39.7 | 13.2 | 15.2 b |
| 'Gingerland' | 45.3 a | 41.8 | 10.8 | 28.8 a |
| P value | .0345 | .4603 | .3088 | .0004 |
| | Blooms (no.) | | Quality Rating[z] | |
| | Intact | De-eye | Intact | De-eye |
| 'UF-15-23' | 0.2 b | 0 | 3.1 | 3.2b |
| 'Gingerland' | 1.7 a | 1.2 | 2.7 | 4.4 a |
| P value | .0446 | .0583 | .3522 | .0004 |

The invention claimed is:

1. A new and distinct cultivar of *Caladium* plant named 'UF-15-23' as illustrated and described herein.

* * * * *